United States Patent [19]

Collins

[11] 4,155,743
[45] May 22, 1979

[54] PLANT GROWTH REGULATION

[75] Inventor: David J. Collins, Crowthorne, England

[73] Assignee: Imperial Chemical Industries Limited, London, England

[21] Appl. No.: 899,394

[22] Filed: Apr. 24, 1978

[30] Foreign Application Priority Data

Apr. 29, 1977 [GB] United Kingdom ............... 18007/77

[51] Int. Cl.$^2$ ............................................. A01N 5/00
[52] U.S. Cl. ........................................ 71/78; 71/123
[58] Field of Search ...................................... 71/78, 123

[56] References Cited

U.S. PATENT DOCUMENTS 3,853,532  12/1974  Rein et al. ................................. 71/78

FOREIGN PATENT DOCUMENTS 4834207  12/1970  Japan ......................................... 71/123

*Primary Examiner*—Catherine L. Mills
*Attorney, Agent, or Firm*—Cushman, Darby & Cushman

[57] ABSTRACT

A method of regulating the growth of tobacco plants, the method consisting essentially of the step of applying to the plants, or to the locus of the plants, a plant growth regulating effective amount of a compound which is 3,5-dinitro-2,6-dimethyl-4-t-butylacetophenone.

2 Claims, No Drawings

PLANT GROWTH REGULATION

This invention relates to a method for regulating the growth of tobacco.

The value of tobacco as a commercial crop is primarily in the leaves of the plant. It is, therefore, desirable to produce plants which achieve maximum growth of leaves on the plant. One method of accomplishing this is to remove the flower and apical bud on the plant. When this is done, the plant tends to develop leaves rather than flowers. When the plants are "topped" by removing the flower and apical bud, side shoots develop on the plant. These shoots are often referred to as suckers. The growth of these suckers is undesirable since it diverts the energy of the plant from the formation of leaves which, as mentioned above, is the type of growth that is desired. To achieve maximum growth of leaves it is, therefore, necessary to remove the suckers. This may be accomplished either by hand or by spraying with a suitable chemical composition. For a variety of quite obvious reasons, treatment with a chemical composition is generally preferred.

Most of the previously available chemical compositions exhibit either contact or systemic activity. For a material which exhibits contact activity to be effective it must contact the part of the plant being treated, e.g. by direct spray or by running down the plant. By comparison, a composition which exhibits systemic activity is absorbed into the plant either through the leaves or roots. Most of the commercially available materials employed for controlling the growth of suckers on tobacco plants exhibit either contact or systemic activity. It would be desirable, to have a compound which exhibits both contact and systemic activity; in this way, more effective long term sucker control could be achieved.

It has now been found that 3,5-dinitro-2,6-dimethyl-4-t-butylacetophenone has plant growth regulating activity in tobacco plants particularly the ability to control sucker growth in tobacco plants. The compound has, it is believed, both contact and systemic activity.

The invention therefore provides a method of regulating the growth of tobacco plants by applying to the plants, or to the locus of the plants, 3,5-dinitro-2,6-dimethyl-4-t-butylacetophenone.

3,5-Dinitro-2,6-dimethyl-4-t-butyl acetophenone is a known compound which is commercially available from a number of sources and is frequently referred to as musk ketone. As such it has been used as an additive in the preparation of perfumes and other fragrances. The compound is known to have herbicidal activity against for example *Digitaria chenopodium* in carrots (Japanese Patent Specification 73/52921) and Japanese millet in radishes (U.S. Pat. No. 3,205,058. Its use on tobacco for any purpose is however not known.

Any type of tobacco may be treated in accordance with the present invention. An example is flue-cured tobacco (*Nicotiania tabacum,* e.g. varieties: Coker 319 and NC2326).

The compound is applied in an amount effective to control the growth of suckers on the tobacco plants being treated. Generally, an amount of active ingredient of 500 to 50,000 p.p.m., preferably 2,000 to 20,000 p.p.m., is effective for this purpose. Treatment may take the form of more than one application of the active ingredient, for example two treatments at 10,000 p.p.m. two weeks apart. The exact amount applied may be varied depending upon a number of circumstances including the type of tobacco, the growing area, and the extent of sucker control required.

The compound can be applied in a number of ways, for example it can be applied, formulated or unformulated, directly to the foliage of the tobacco plants. It can be sprayed on, dusted on or applied as a cream or paste formulation, or it can be applied in the form of a vapour. Application can be to any part of the plant, for example to the foliage, stems, branches or roots, or to soil surrounding the roots.

The compound is preferably used in the form of compositions.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient in an organic solvent optionally containing wetting, dispersing or emulsifying agent and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The active compound can be mixed in the dry state with a pyrotechnic mixture to form a composition suitable for generating in enclosed spaces a smoke containing the compounds. Alternatively, the compounds may be used in a microencapsulated form.

By including suitable additives, for example additives for improving the distribution, adhesive power and resistance to rain on treated surfaces, the different compositions can be better adapted for various utilities.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient, the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 15-60%, by weight of the active ingredient. These concentrates suitably contain organic acids (e.g. alkaryl or aryl sulphonic acids such as xylenesulphonic acid or dodecylbenzenesulphonic acid) since the presence of such acids can increase the solubility of the active ingredient in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention can comprise also other compound(s) having biological activity, e.g. compounds having fungicidal, plant growth regulating, herbicidal or insecticidal activity. The compositions can also comprise stabilising agent(s), for example epoxides (e.g. epichlorhydrin).

The following Examples illustrate the invention.

EXAMPLE 1

The following composition (Composition 1) was prepared:

| | % w/v |
|---|---|
| 3,5-dinitro-2,6-dimethyl-y-t-butyl acetophenone | 20 |
| Acetophenone | 20 |
| Arylan CA* | 2.5 |
| Lubrol N13 | 2.5 |
| Aromasol | q.v. |

*Calcium dodecyl benzene sulphonate

This emulsifiable concentrate composition, containing 10% w/v of the wetter Lissapol NX, was sprayed on to the stems of tobacco plants. The apices of the plants were removed one day after spraying. Assessment of the sucker weight was made two weeks after spraying. The results are shown in Table I below:

TABLE I

| TREATMENT | RATE (ACTIVE INGREDIENT) | SUCKER WT (g) | SUCKER WT AS % CONTROL |
|---|---|---|---|
| Test Composition | 2500 ppm | 0 | 0 |
| Control | — | 12.25 g | 100 |

EXAMPLE 2

The following composition (Composition 2) was prepared:

| | % w/v |
|---|---|
| 3,5-dinitro-2,6-dimethyl-4-4-t-butyl acetophenone | 20 |
| Aerosol OT | 15 |
| Octanol | 15 |
| Acetophenone | q.v. |

Composition 2 was tested on tobacco in the field at Goldsboro, North Carolina, USA. Also tested were the commercially available tobacco desuckering agents, maleic hydrazide and Chiptac (a mixture of fatty alcohols and containing 78% of decanol).

Tobacco plants were transplanted (7500 per acre) from a tobacco bed on May 10, 1976. The first contact treatments were applied on July 8, 1976, when the blossoms were at the early button stage. This was determined when 70% of the plants were at this stage of flowering.

Contact sprays of Composition 2 and Chiptac were applied on July 8, 1976 as coarse sprays using a single TG5 full cone nozzle at 55 gpa (approximately 20 ml/plant) and a pressure of 15 psi. The spray was directed at the terminal bud to afford run-off down the length of the stem and contact with suckers in each leaf axil. A similar arrangement was used on July 21 for the second application with Composition 2 when two applications were made.

Systemic maleic hydrazide sprays were applied as a fine foliar spray directed at the top half of the leaves using a TC3 cone nozzle at 25 gpa and 40 psi. Applications were conducted alone on July 9, sequentially following Chiptac on July 14 and sequentially following Composition 2 on July 21. The five day delay with Composition 2 was due to its greater efficacy over Chiptac.

The plants were topped (terminal growing point removed) 48 hours following application of the first contact sprays. This is the practice normally used by growers. Leaves were primed (harvested) at regular normal intervals throughout the test period.

After about 7 weeks after the first application, the suckers were collected, counted and weighed.

The results are shown in Table II below.

TABLE II

| TREATMENT | RATE (ppm) | NUMBER OF SUCKERS | SUCKER FRESH WEIGHT(S) |
| --- | --- | --- | --- |
| Single treatment with Composition 2 | 20,000 | 0.4 | 49 |
| | 10,000 | 0.7 | 93 |
| Two treatments with Composition 2 | 20,000 + 5,000 | 0.5 | 10 |
| | 10,000 + 10,000 | 0.1 | 1 |
| Treatments with Composition 2 followed by maleic hydrazide | 20,000 + 5,000 | 0.3 | 37 |
| | 20,000 + 2,500 | 0.1 | 30 |
| | 20,000 + 1,250 | 0.8 | 43 |
| Maleic hydrazide | 5,000 | 7.2 | 315 |
| | 2,500 | 7.8 | 599 |
| | 1,250 | 6.3 | 601 |
| Chiptac | 20,000 | 3.0 | 393 |
| Chiptac followed by maleic hydrazide | 20,000 + 5,000 | 1.6 | 42 |
| Control | | 5.3 | 527 |

The results show that the composition containing 3,5-dinitro-2,6-dimethyl-4-t-butylacetophenone is more active in controlling suckers than the two commercially available tobacco desuckering agents.

I claim:

1. A method of controlling the formation of suckers in tobacco plants, the method consisting essentially of the step of applying to the plants, or to the locus of the plants, an effective amount of 3,5-dinitro-2,6-dimethyl-4-t-butylacetophenone.

2. A method as claimed in claim 1 wherein the tobacco plants are of the species *Nicotiania tabacum*.